(12) United States Patent
Sandoval et al.

(10) Patent No.: US 6,330,830 B1
(45) Date of Patent: Dec. 18, 2001

(54) TENSION/COMPRESSION FATIGUE CRACKING GRIPS

(76) Inventors: David Lynn Sandoval, P.O. Box 441, Truchas, NM (US) 87578; Loren A. Jacobson, 7416 Old Santa Fe Trail, Santa Fe, NM (US) 87505

( * ) Notice: Subject to any disclaimer, the term of this patent is extended or adjusted under 35 U.S.C. 154(b) by 0 days.

(21) Appl. No.: 09/366,089

(22) Filed: Aug. 3, 1999

(51) Int. Cl.⁷ ............................................. G01N 3/02
(52) U.S. Cl. ........................................... 73/856; 73/860
(58) Field of Search ......................... 73/860, 859, 858, 73/857, 856, 852, 49.8, 49.1

(56) References Cited

U.S. PATENT DOCUMENTS

| | | | |
|---|---|---|---|
| 4,276,771 | * 7/1981 | Wesch, Jr. | 73/49.8 |
| 4,721,000 | * 1/1988 | Scanlon | 73/859 |
| 4,875,376 | * 10/1989 | Fischer | 73/852 |
| 5,948,994 | * 9/1999 | Jen et al. | 73/856 |

OTHER PUBLICATIONS

S–200 Grade Beryllium Fracture Toughness Properties, W. O. Shabbits and W.A, Logsdon, Journal of Testing and Evaluation, vol. 1, No. 2, Mar. 1973, pp. 110–118.

* cited by examiner

Primary Examiner—Benjamin R. Fuller
Assistant Examiner—Maurice Stevens
(74) Attorney, Agent, or Firm—DeWitt M. Morgan

(57) ABSTRACT

A pair of grips for holding a specimen which includes a pair of through openings for receiving tension pins and a pair of spaced apart, parallel edges. Each of the grips includes a pin, a Davis adjustable key, and a housing. The Davis adjustable key includes a key housing, a movable key portion and a mechanism to move the key portion relative to the key housing. The housing includes a bore for receiving the Davis adjustable key, a bore for receiving the pin, and a slot for receiving that portion of the specimen which includes the through opening and the edge. The Davis adjustable key bore and said pin bore are substantially parallel to each other. The slot is substantially perpendicular to and completely bisecting the pin bore. The slot also partially intersects the Davis adjustable key bore to, when the specimen is received in the slot, the pin received in the through opening and the in bore, and the Davis adjustable key is received in the Davis adjustable key bore, permit the moveable key portion to be moved into engagement with the edge.

5 Claims, 5 Drawing Sheets

TENSION/COMPRESSION FATIGUE CRACKING GRIPS

BACKGROUND OF THE INVENTION

This invention relates to grips which are used to hold a compact fracture specimen while it is loaded in tension and compression by a hydraulic load frame.

Initiation and controlled propagation of cracks must be produced in various types of materials such as beryllium, ceramics, and various steels under tension/compression cycling in order for subsequent fracture toughness or crack growth rate testing to be valid. Such testing is described in S-200 Grade Beryllium Fracture Properties, *Journal of Testing and Evaluation*, JTEVA, Vol. 1, No. 2, March 1973, pp. 110–118.

The above described testing may be carried out with, for instance, an 810 Material Test System, manufactured by MTS, Inc., Eaton Prairie, Minn. However, the sample holding grips supplied by MTS are not suitable for holding the specimen to be tested in both tension and compression. The standard grips allow for only tensile loading of the specimen through two tension pins that are of smaller diameter than corresponding holes in the specimen. It is the clearance of the pins that pass through holes in the specimen that precludes cyclic loading of the specimen in both tension and compression.

The use of set screws to apply pressure to the top and bottom edges of the specimen, in order to achieve the compressive part of the loading cycle, are not effective. The set screws are not capable of producing an adequate pressure on the specimen to prevent vibration during the loading cycles. This will lead to frequent loosening of the assembly which, in some cases, will result in the tension pins falling out and the test terminating early. The use of an adjustable pin, as suggested in the Journal of Testing and Evaluation, supra, also proved ineffective. Vibration during testing resulted in a loosening of the tension pins.

Accordingly, it is an object of the present invention to provide grips for tension/compression cycle testing, which hold the specimen tightly in position and do not loosen during the testing cycle.

SUMMARY OF THE INVENTION

A pair of grips for holding a specimen which includes a pair of through openings for receiving tension pins and a pair of spaced apart, parallel edges. Each of the grips includes a pin, a Davis adjustable key, and a housing. The Davis adjustable key includes a key housing, a movable key portion and a mechanism to move the key portion relative to the key housing. Each housing includes a bore for receiving the Davis adjustable key, a bore for receiving the pin, and a slot for receiving that portion of the specimen which includes the through opening and the edge. The Davis adjustable key bore and the pin bore are substantially parallel to each other. The slot is substantially perpendicular to and completely bisects the pin bore. The slot also partially intersects the Davis adjustable key bore to, when the specimen is received in the slot, the pin received in the through opening (of the specimen) and the in the bore (of the housing) and the Davis adjustable key is received in the Davis adjustable key bore, permit the moveable key portion to be moved into engagement with the edge. The Davis adjustable key bore is oblong and includes two substantially parallel sides. The Davis adjustable key also includes two substantially parallel sides. The spacing between said parallel sides on the Davis adjustable key is slightly less than the spacing between the parallel sides of the David adjustable key bore to provide a close fit therebetween.

The method of holding the specimen for testing in both tension and compression, includes the steps of inserting a tension pin in each of the through openings, and moving the movable key portion of each of a pair of Davis adjustable keys into engagement with each of the edges.

DESCRIPTION OF THE PREFERRED EMBODIMENT

Figure 1:
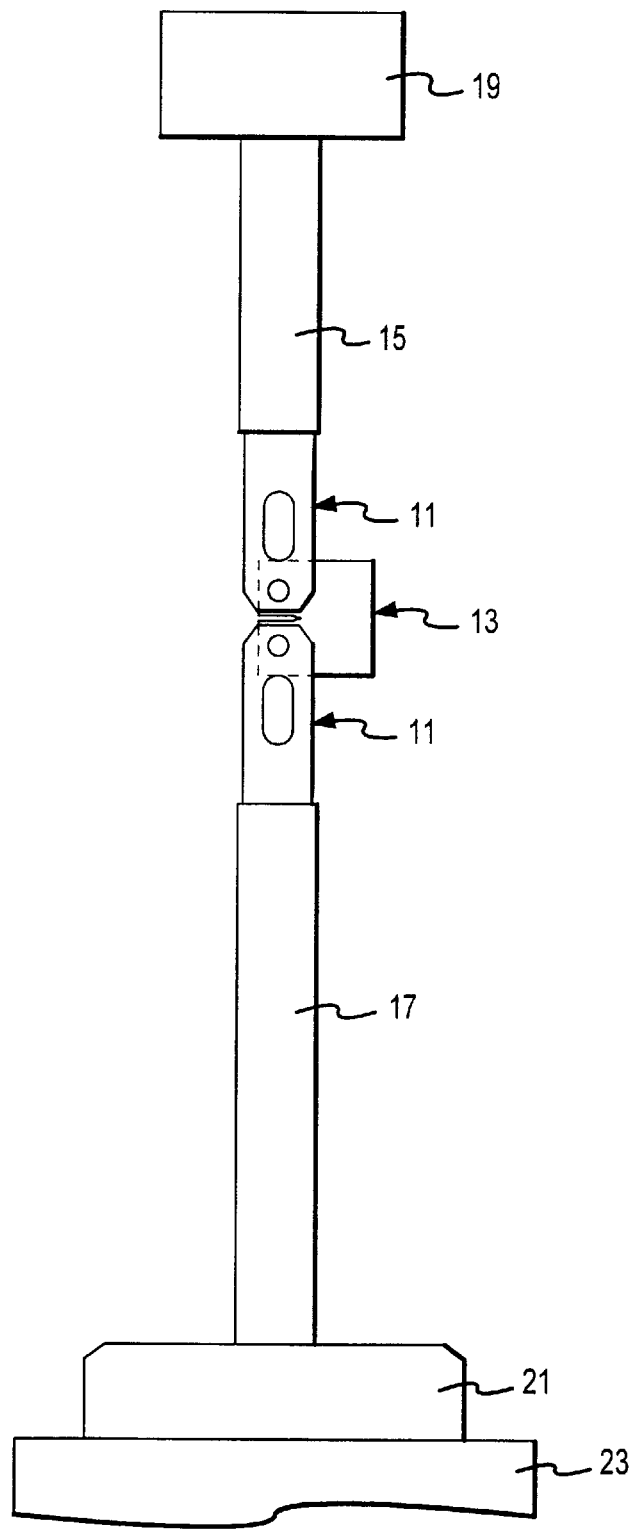
FIG. 1 is a plain view of the sample grips of the present invention, assembled with the sample and the MTS 810 Material Test System.

In FIG. 1, grips 11 are shown assembled with sample 13 and extension rods 15 and 17. In turn, rod 15 is attached to ram 19 of a hydraulic load frame, such as the MTS 810. Rod 17 is connected to load cell 21 which is, in turn, connected to table 23 of the hydraulic load frame. As those skilled in the art will appreciate, the use of extension rods is optional. As assembled with grips 11, sample 13 can alternately be cycled in tension and compression in order to produce the desired controlled pre-crack.

Figure 2:
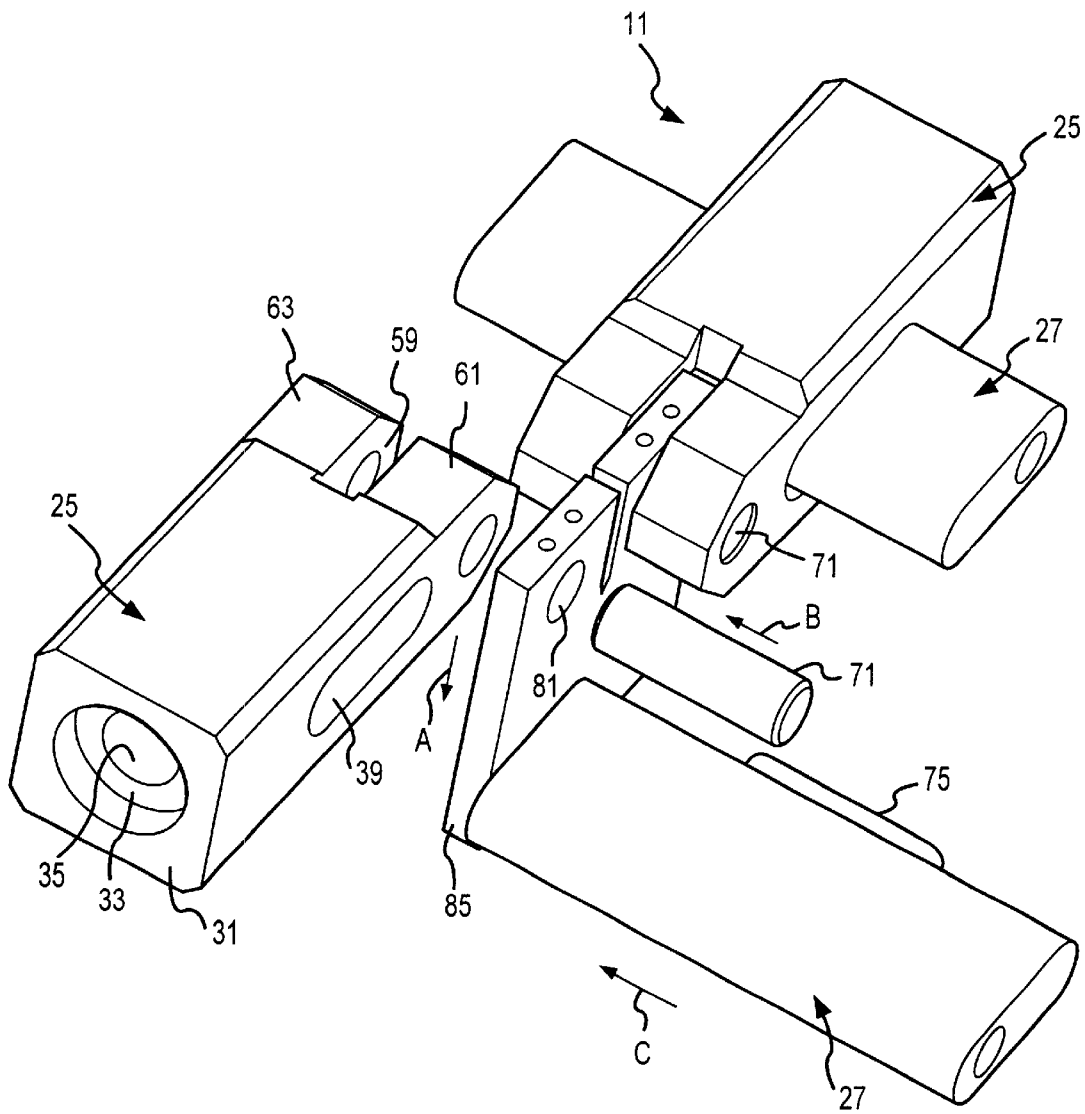
FIG. 2 is a partially exploded perspective view of the grips of the present invention with a sample to be tested.

As best illustrated in FIGS. 2–5, each grip 11 includes a housing 25 and a Davis adjustable key 27. Housing 25, which is typically fabricated of steel (e.g., Vascomax 250), includes a base 31 having a counter sunk shoulder 33, and a threaded bore 35 having a counter sunk recess 37. In the illustrated embodiment, one of the threaded ends of rod 15 or 17 (not shown) is received in bore 35. Countersunk recess 37 is provided so that there is no tightening on the threads themselves. Most threads have a wide tolerance which can cause misalignment. Recess 37 at the beginning of threads 35 is to allow a surface of contact between the extension rod and housing 25 for alignment purposes. Housing 25 also includes an elongated through bore 39 which is designed to receive Davis adjustable key 27. With reference to FIGS. 4A and 5B, the spacing between parallel surfaces 41 and 43 of bore 39 is just slightly greater the corresponding spacing between parallel surfaces 45 and 47 of Davis adjustable key 27. To keep Davis adjustable key 27 properly aligned in bore 39, so as to prevent specimen 13 from being clamped on at an irregular angle (or cocked), there should be a clearance of, approximately, 0.001 inches between opposing surfaces 41, 45 and 43, 47. In operation, arcuate or curved surface 53 rides on arcuate or curved surface 49. Between curved surfaces 51 and 55 there is a gap of, approximately, 0.064 inches. Housing 25 also includes a cylindrical through bore 57 and a sample receiving slot 59. The principal axis of bore 57 is parallel with the principal axis of bore 39. As best illustrated in FIG. 4B, slot 59 bisects the upper end of housing 25 and bore 57 to form two ear-like projections 61 and 63. Slot 59 is perpendicular to bore 57. As best illustrated in FIGS. 2 and 4A, the bottom 65 of slot 59 intersects arcuate surface 51, so that, when assembled, a portion of sample 13 will be received in bore 39. The diameter of bore 57 is slightly greater than the diameter of pins 71.

Figure 5B:
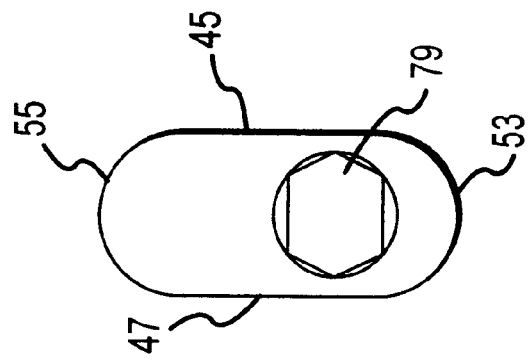
FIGS. 5A and 5B are the side and end views of a Davis adjustable key incorporated in the grips of the present invention.
Figure 5A:
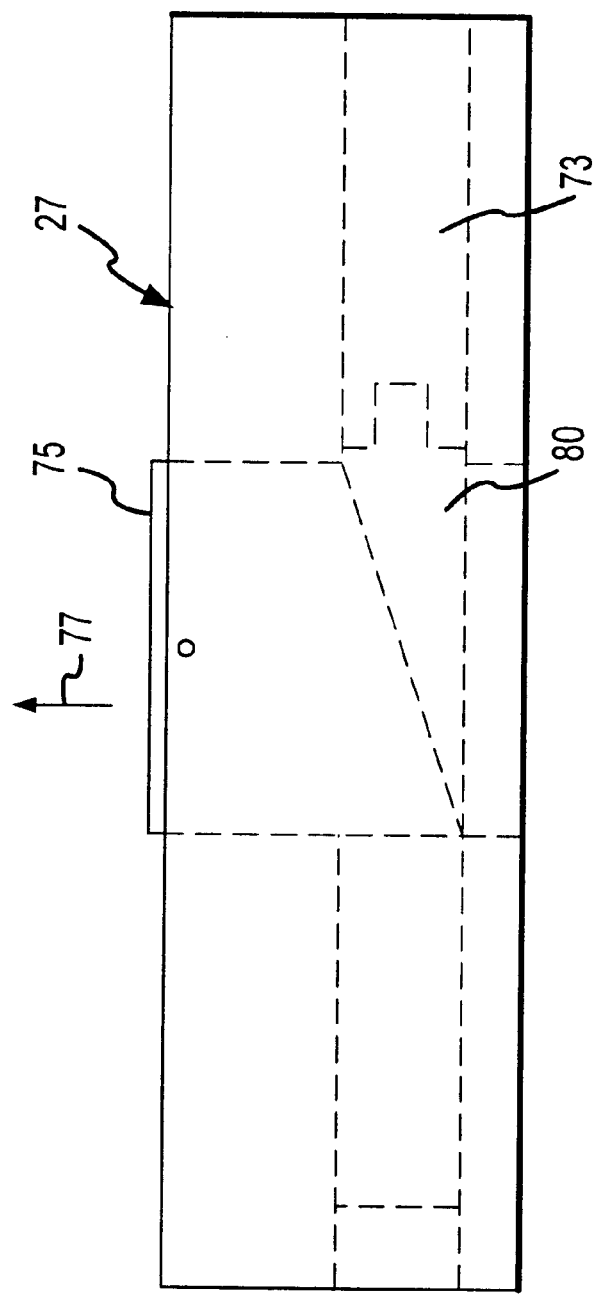

The Davis adjustable key 27 is best illustrated in FIGS. 5A and 5B. Key 27 includes a housing 73, having exterior surfaces 45, 47, 53, and 55, as described above. Key 27 also includes a key portion 75 which is movable in a direction indicated by arrow 77 by turning hex set screw 79 in a clockwise direction. This rotation, in turn, moves wedge 80, which is coupled to set screw 79. Davis adjustable keys are available from Giddings and Lewis.

Sample 13 is, basically, rectangular and has a thickness of either ¼ or ½ inches. It includes spaced apart cylindrical bores 81 and a slot 83. Bores 81 have the same diameter as bore 57. Slot 83 is provided to allow for a place for the crack to start. Sample 13 also includes opposed edges 85.

Figure 3:
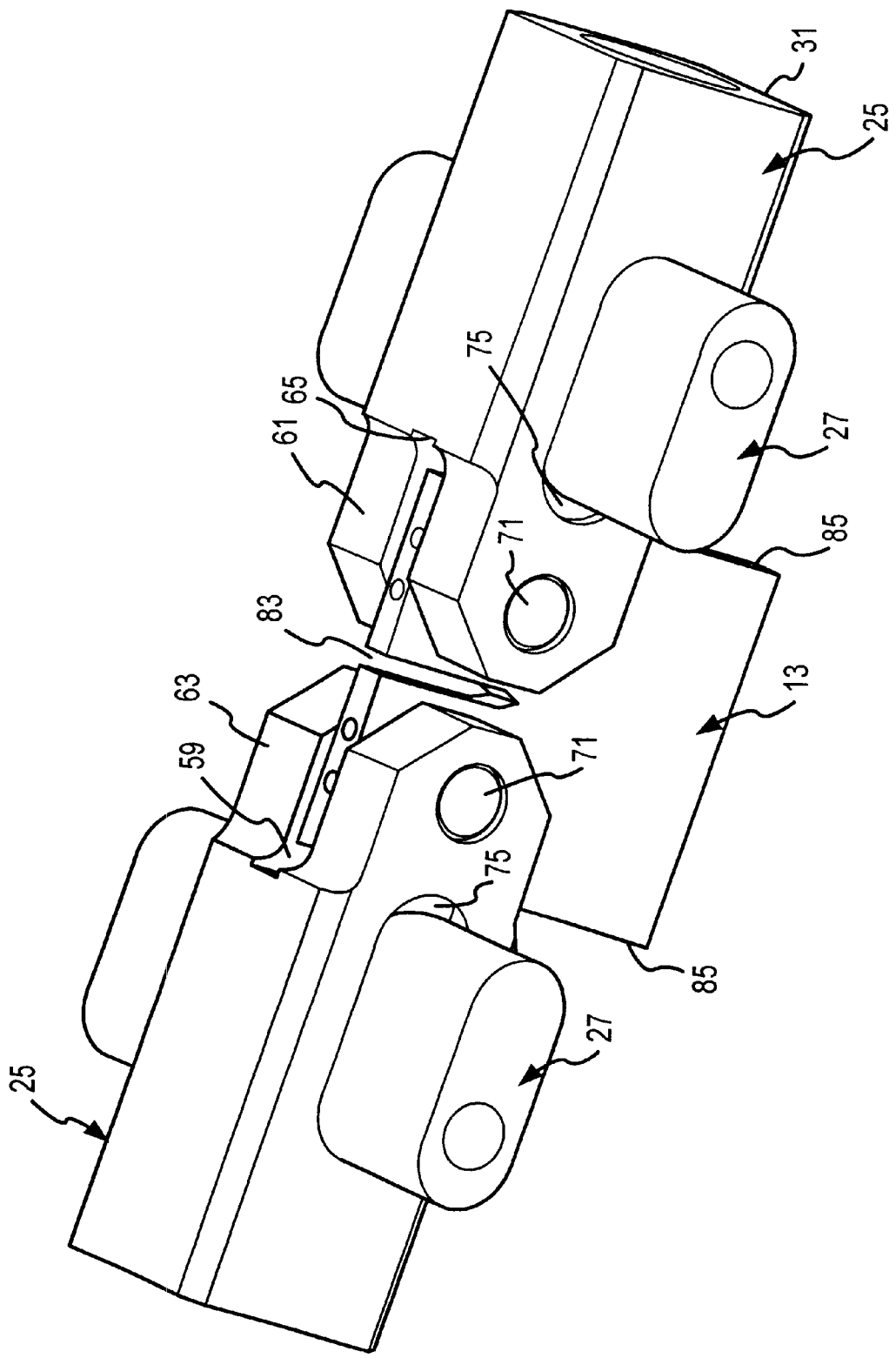
FIG. 3 is a perspective view of the grips assembled with a sample to be tested.
Figure 4A:
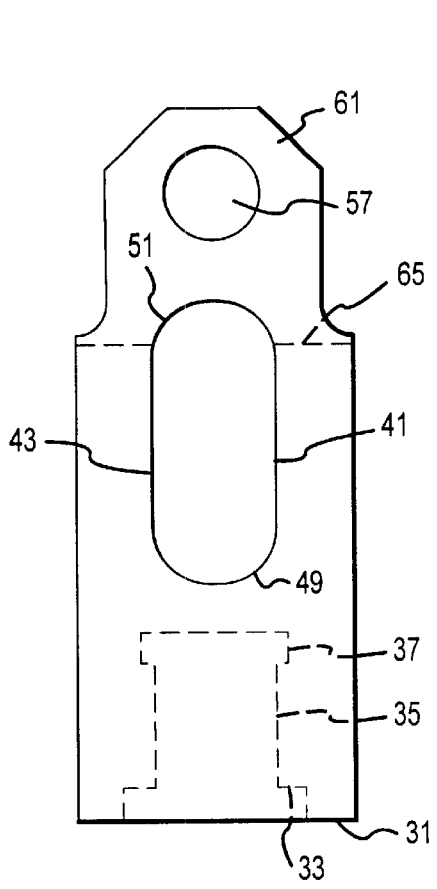
FIGS. 4A, 4B, and 4C are the front, side and bottom views of one of the grip housings of the present invention.
Figure 4B:
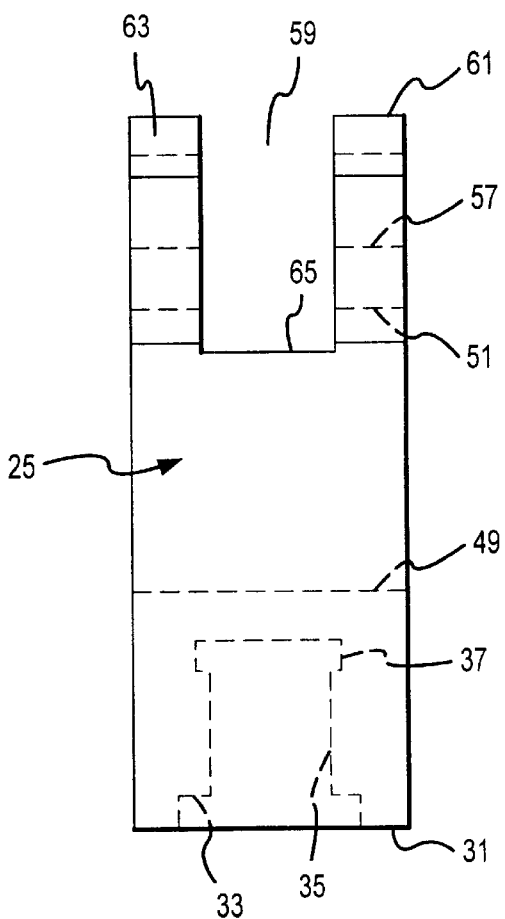
Figure 4C:
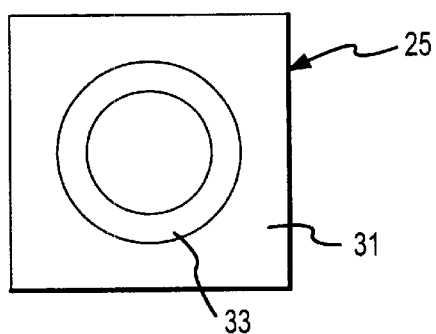

The relationship between grips 11, including Davis keys 27, sample 13 and pins 71 is best illustrated in FIGS. 1, 2 and 3. In operation rods 15 and 17 are attached to, respectively, ram 19 and load cell 21. Housings 25 are then attached to the opposed ends of rods 15 and 17 and tightened in place with slots 59 in alignment with each other. Specimen 13 is then slid into slots 59 of housings 25 such that bores 81 align with bores 57 and edges 85 are, approximately, parallel with bottoms 65. Pins 71 are then inserted in the two sets of aligned bores. With specimen 13 held in place by pins 71, a slight load, in tension, of about 15 lbs., is applied to specimen 13. Davis keys 27 are then inserted into bores 39 with key portions 75 positioned to engage that portion of each of edges 85 which is exposed in each bore 39 due to the intersection of slot 59 with surface 51 of bore 39. Davis adjustable keys 27 are then tightened, with each of key portions 75 engaging its opposing edge 85. Arrows A, B and C show the movement of: housing 25 relative to sample 13; pin 71 relative to ear 61, then bore 81, and then ear 63; and Davis adjustable key relative to housing 25. FIG. 3 illustrates the final relation ship among the assembled parts.

Whereas the drawings and accompanying description have shown and described the preferred embodiment of the present invention, it should be apparent to those skilled in the art that various changes may be made in the form of the invention without affecting the scope thereof.

What is claimed is:

1. A grip for holding a specimen, said specimen including a through opening for receiving a pin and an edge, said grip comprising:
    a. a pin;
    b. a Davis adjustable key, said Davis adjustable key including a key housing, a movable key portion and means to move said key portion relative to said key housing; and
    c. a housing, said housing including a bore for receiving said Davis adjustable key, a bore for receiving said pin, and a slot for receiving that portion of said specimen which includes said through opening and said edge, said Davis adjustable key bore and said pin bore being substantially parallel to each other, said slot being substantially perpendicular to and completely bisecting said pin bore, said slot also partially intersecting said Davis adjustable key bore, when said specimen is received in said slot, said pin received in said through opening and said pin bore, and said Davis adjustable key is received in said Davis adjustable key bore, said moveable key portion being moveable into engagement with said edge.

2. The grip of claim 1, wherein said housing also includes means to secure said housing to a hydraulic load frame.

3. The grip of claim 1, wherein said Davis adjustable key bore is oblong and includes two substantially parallel sides, and wherein said Davis adjustable key also includes two substantially parallel sides, the spacing between said parallel sides on said Davis adjustable key being slightly less than the spacing between said parallel sides of said Davis adjustable key bore, to provide a close fit there between.

4. A pair of grips for holding specimen, said specimen including a pair of through openings for receiving tension pins and a pair of spaced apart, parallel edges, each of said grips comprising:
    a. a pin;
    b. a Davis adjustable key, said Davis adjustable key including a key housing, a movable key portion and means to move said key portion relative to said key housing; and
    c. a housing, said housing including a bore for receiving said Davis adjustable key, a bore for receiving said pin, and a slot for receiving that portion of said specimen which includes said through opening and said edge, said Davis adjustable key bore and said pin bore being substantially parallel to each other, said slot being substantially perpendicular to and completely bisecting said pin bore, said slot also partially intersecting said Davis adjustable key bore, when said specimen is received in said slot, said pin received in said through opening and said pin bore, and said Davis adjustable key is received in said Davis adjustable key bore, said moveable key portion being movable into engagement with said edge.

5. A method of holding a specimen for testing in both tension and compression, said specimen including a pair of parallel through openings and a pair of spaced apart parallel edges, said method including the steps of inserting a tension pin in each of said through openings moving the movable key portion of each of a pair of a Davis adjustable key into engagement with each of said edges.

* * * * *